United States Patent [19]
Sharma

[11] Patent Number: 6,036,493
[45] Date of Patent: Mar. 14, 2000

[54] DENTAL BLEACHING SYSTEM AND METHOD

[75] Inventor: Brahma Sharma, Louisville, Colo.

[73] Assignee: Ad Dent Inc., Danbury, Conn.

[21] Appl. No.: 09/121,040

[22] Filed: Jul. 23, 1998

[51] Int. Cl.$^7$ .................................................. A61C 15/00
[52] U.S. Cl. ........................... 433/216; 433/215; 424/49; 424/53
[58] Field of Search ..................................... 433/215, 216; 424/49, 53; 252/186.26–186.29

[56] References Cited

U.S. PATENT DOCUMENTS

| | | | |
|---|---|---|---|
| 4,554,154 | 11/1985 | White | 424/16 |
| 4,941,751 | 7/1990 | Muhlbauer | 366/176 |
| 5,000,942 | 3/1991 | Libin | 424/53 |
| 5,032,178 | 7/1991 | Cornell | 106/35 |
| 5,076,791 | 12/1991 | Madray | 433/215 |
| 5,122,365 | 6/1992 | Murayama | 424/49 |
| 5,376,006 | 12/1994 | Fisher | 433/215 |
| 5,409,631 | 4/1995 | Fisher et al. | 252/186.25 |
| 5,425,953 | 6/1995 | Sintov et al. | 424/404 |
| 5,645,428 | 7/1997 | Yarborough | 433/215 |
| 5,928,628 | 7/1999 | Pellico | 424/49 |

*Primary Examiner*—John J. Wilson
*Assistant Examiner*—Melba Bumgarner
*Attorney, Agent, or Firm*—E. Lieberstein

[57] ABSTRACT

A dental bleaching system and method having two separated components adapted to be dispensed from a single dispenser as a mixed viscous dental bleach composition. The first component comprises aqueous hydrogen peroxide and the second component includes a gelling agent, catalyst, a pH alkaline buffer, a redox color indicator adapted to oxidize in the presence of a peroxide from a visible color into a neutralized color and a second dye stable in the presence of a peroxide with the concentration of the redox color indicator selected relative to the second dye such that the redox color will be predominant during the bleaching operation and the second dye will be predominant at the end of a controlled time period corresponding to when the bleaching treatment may be discontinued.

17 Claims, No Drawings

DENTAL BLEACHING SYSTEM AND METHOD

FIELD OF THE INVENTION

The present invention relates to a two component dental bleaching system and method for bleaching human dentition.

BACKGROUND OF THE INVENTION

Tooth bleaching or "whitening" was in the past limited to the treatment of teeth discoloration which was primarily an affliction of middle-aged and older dental patients where teeth discoloration was prevalent. Discolored teeth results generally from intrinsic or extrinsic stains. Intrinsic stains are attributable to highly mineralized water, particularly water containing a high concentration of iron or fluoride which cause teeth to discolor upon being absorbed into the body or from tetracycline stains, which occur, in utero during the third trimester of pregnancy. Extrinsic stains are diet related and result primarily from smoking or drinking coffee and/or tea.

The bleaching of teeth has now become an accepted cosmetic practice of young patients as well as older patients who desire to give themselves a more youthful appearance by whitening their teeth. The traditional bleaching procedure of using a strong concentrate of hydrogen peroxide, typically a bleaching solution of 35% hydrogen peroxide, is still in current practice in the dental office either by the dentist or dental practitioner using a rubber dam to protect the gingiva. During this process the hydrogen peroxide may be heated externally to raise the temperature of the reaction and speed up the bleaching process. The external application of heat activates the dissociation of the peroxide.

It is however now more commonplace to carry out the bleaching process using a peroxide gel as the bleaching agent both in the dental office and particularly where the bleaching process is intended to be self applied by the patient in the home. The peroxide gel generally consists of a carbamide or a hydrogen peroxide composite composition. When bleaching is carried out in the dental office a source of heat may also be applied from a dental curing light or other light source such as a laser. The rubber dam is still used to protect the gingiva when the bleaching operation is carried out in the dental office. For home use bleaching applications a custom made bite tray is used to accommodate self treatment by the patient. For home application the bleaching agent consists of a lower concentrate peroxide such as 10% carbamide peroxide.

The drawbacks of present day bleaching systems both for home use and in the dental office are numerous. For example, the requirement of using an external heat source as a means of activation usually requires both the dentist and a dental assistant to spend a considerable amount of time with the patient while the bleaching process takes place. This is not an economical use of the dentists' time. As such, home bleaching has assumed a greater role where the dentist provides instruction and supervision only. Even when the bleaching operation is practiced in the dental office, reliance upon a 35% liquid hydrogen peroxide concentrate is dangerous despite the use of a rubber dam since it can spill or splash and the droplets that are dispensed are imprecise. Alternatively, mixing a powder and a liquid is inaccurate, time consuming and messy. Even systems that contemplate the use a bleaching gel instead of a liquid depend upon the normal breakdown of hydrogen peroxide which is a relatively slow operation and accordingly require additional energy from an external heat source such as a dental curing light or a laser.

A preferred dental bleaching system for use by a dental practitioner in the dental office or for self application by a patient at home should require little, if any, individual attention, operate over a controlled relatively short time period and most importantly, particularly for home use, provide an automatic indication of when the bleaching treatment can be terminated i.e., when the bite tray may be removed for replacement at a later time with a fresh bleaching composition. A bleaching system which provides some of the above features is taught in U.S. Pat. No. 5,032,178. However, the bleaching composition taught in this patent is intended to be activated using an externally applied heating source such as a dental light to avoid a bleaching time period which is extraordinarily long. In addition, although the redox color indicator guinea green is identified in the above patent to react during the bleaching operation so as to provide the patient with an indication of the termination of the bleaching operation, in fact, it neutralizes to become colorless which, as a practical matter, is not readily discernable or distinguishable from the color of tooth enamel. More specifically guinea green turns the bleach composition from green to white which does not contrast well against the white color of tooth enamel. Furthermore, the bleaching composition is intended to be hand mixed from a powder and liquid $H_2O_2$ formulation prior to use which is inaccurate and not particularly safe or convenient particularly for home use.

SUMMARY OF THE INVENTION

The dental bleaching system of the present invention is a two component bleaching system which bleaches a tooth or teeth over a controlled relatively short time period and provides a distinguishable color which is visibly apparent to the naked eye when the bleaching treatment has terminated. In addition, no intervention is required of the dental practitioner or patient during the bleaching operation and the system does not require external activation i.e., no external heat or light source is needed. Moreover, the two component system may be incorporated into any known capsule mixing device as taught for example in U.S. Pat. No's. 4,941,751 and 5,172,807 or a syringe capable of storing two components isolated from each other as taught for example in U.S. Pat. No's. 4,538,920 and 4,767,026 whereupon the two components may be brought into contact with one another and intermixed by means of a dental amalgamator or a static mixing element in the dispenser and then discharged from the dispenser. In this way the bleaching operation is initiated only at the time of use and without the need for individual handling of the components or mixing the separated components on a mixing pad i.e., the bleaching composition can be applied directly to the teeth from a dispensing device as taught for example in U.S. Pat. No. 5,306,147 or loaded into the dental tray from the dispenser for self application. The two components can each be formulated to have a viscous gel constituency or formulated as a powder-liquid combination which upon intermixing combine to form a viscous gel like consistency. In each instance the two components are pre-measured and intermixed in proper proportion to one another for direct use either by the patient or dental practitioner without the need to make hand contact with the materials during formulation or dispensing.

The dental composition of the present invention is adapted to be dispensed from a mixing dispenser as a single intermixed viscous dental bleach composition. In a preferred embodiment the dental composition includes a first component having a viscous gel like consistency consisting essentially of hydrogen peroxide and a gelling agent and a second component having a viscous gel like consistency comprising an aqueous composition including a gelling agent, a catalyst, a pH alkaline buffer, a redox color indicator which will oxidize in the presence of a peroxide such as guinea green or phenolphthalein and the like and a second dye stable in the presence of a peroxide such as Pylakor Acid Red LX6514, Pylaklor Peacock Blue, Pylaklor Yellow S-184 and Beet Powder 03600 Vegetable Color or any other dye stable in peroxide which will be subordinate to the redox color indicator during bleaching and provide a distinct visible color at the end of the bleaching operation. The oxidizable redox color indicator should be in a proportion to the second dye such that the color of the redox color indicator will predominant until the bleaching treatment is substantially complete.

The invention also involves a method of dispensing a two component bleaching composition as a viscous gel directly upon a tooth or teeth to be bleached. In one preferred method the first component is hydrogen peroxide and the second component is a formulation consisting essentially of a gelling agent, a pH alkaline buffer, a catalyst and a color indicator such that upon combining the two components one distinct visible color appears to the naked eye during the bleaching treatment and another when the bleaching treatment has effectively terminated. In this method each component is placed in a capsule having two compartments separated by a membrane so that each component is isolated from each other with the capsule including a movable element which breaks the membrane upon being manually depressed so that the separated components come into contact with one another. Thereafter the capsule is placed in a dental amalgamator to intermix the first and second components to form a viscous gel and the capsule is then placed in a dispensing syringe for dispensing the viscous gel directly onto the tooth or teeth to be bleached. The color indicator consists of a redox color indicator adapted to oxidize in the presence of a peroxide from a visible color into a neutralized color and a second dye stable in the presence of a peroxide with the concentration of the redox color indicator selected relative to the second dye such that the redox color will be predominant during the bleaching operation and the second dye will predominant at the end of a controlled time period corresponding to when the bleaching treatment may be discontinued.

DETAILED DESCRIPTION OF THE PREFERRED EMBODIMENT

The dental bleaching system of the present invention is a two component system adapted to be used in conjunction with a dental mixing capsule or static mixing syringe capable of storing two components isolated from each other and discharging them in mixed form. Capsule dispensers of this type are well known for use in the dental field primarily in conjunction with the preparation of dental cements and filling materials. Static mixing syringes are used for dispensing impression materials and are available for industrial use. Each of the components of the dental bleaching system of the present invention may be formulated as a gel with a preferred composition as hereafter indicated in Table I or as a powder liquid combination with a preferred composition as hereafter indicated in Table II.

TABLE I

| Constituent | Range/(Percent) |
|---|---|
| COMPONENT A (PEROXIDE GEL) | |
| Hydrogen Peroxide | 10–35% |
| Amorphous Fumed Silica | 20–22 g ± 10% |
| COMPONENT B (ACTIVATOR GEL) | |
| Distilled water | 75–90% |
| Amorphous Fumed Silica | 4.75–25% |
| Manganese Citrate | 4.75–15% |
| Triethanolarnine | .2–5% |
| Sodium Benzoate | .2–5% |
| Guinea Green B.GA | .01–1% |
| LX6514 Pylakor, Acid Red | .01–.5% |

The aforementioned ingredients of component A and component B represent the preferred gel-gel formulation of the present invention. For the dental office component A will preferably include 20–35% aqueous hydrogen peroxide and a gelling agent. The preferred gelling agent of the present invention is silica particularly amorphous fumed silica but any other gelling or thickening agent may be used such as CMC (carboxy methyl cellulose), poly carboxylates for example Carbopol and other silica based thickeners inclusive of precipitated or ground clay.

For the home application component A will preferably include 10–15% aqueous hydrogen peroxide and amorphous fumed silica. In each case the hydrogen peroxide constituent is the bleaching agent. A suitable 35% hydrogen peroxide gel composition includes 200 g±10% of 35% hydrogen peroxide and 20 g±10% of amorphous fumed silica. A suitable 15% aqueous hydrogen peroxide gel composition includes 100 g±10% of 35% hydrogen peroxide; 110 g±10% distilled water and 20 g±10% amorphous fumed silica.

Component B is the aqueous activator for component A with the amorphous fumed silica constituent representing the preferred gelling agent and with the manganese citrate constituent functioning as the preferred catalyst for hydrogen peroxide to accelerate the generation of free hydroxy radicals without externally applied heat. Other positive catalysts which will accelerate the decomposition of hydrogen peroxide may be substituted for manganese citrate such as manganese sulfate. However, the presence of manganese citrate is believed to cause the generation of free hydroxy radicals which accelerates the reaction rate and the generation of nascent oxygen which functions as a strong bleaching agent to whiten teeth. Accordingly, this composition does not require an external heating source since the bleaching action is not solely dependent on the normal breakdown or dissociation of peroxide. In the conventional system the bleaching action is normally activated by the external application of heat through a curing light or laser source. It should be understood that although an externally applied heat source or source of light energy is not essential to the present invention it may still be used with the bleaching composition of the present invention if it is desired to further accelerate the bleaching process or to render the catalyst optional. However, the addition of a catalyst is preferred.

The constituent triethanolamine is a preferred pH alkaline buffer and is used to provide control over the stability and rate of the reaction in the gel-gel composition of Table I. Although triethanolamine is preferred any pH alkaline buffer may be used although for the gel-gel composition an alkanolamine is preferred. Other alkaline buffers such as sodium, potassium or other alkaline metallic compounds particularly hydroxides, carbonates and bicarbonates and the like may be used including to a lesser extent sodium hydroxide. The higher the pH of the composition the faster the reaction. Control over pH is achieved by the proportion of the constituents in the composition or by the addition of a buffer. The overall pH range is 2.6–8 with a preferred pH range of between 4–7. Control over pH also minimizes tooth enamel etching and potential gingival irritation. In the preferred pH range the total bleaching time can be controlled to occur within 3–10 minutes from the onset of activation upon mixing components A and B. The incorporation of sodium benzoate is important as a preservative to inhibit the growth of bacteria. Any known common food grade preservative that will control bacterial contamination in water may be used as a substitute for sodium benzoate.

The use of a redox color indicator which is capable of being oxidized by hydrogen peroxide such as guinea green or phenolphthalein and the like and a dye which is stable in the presence of hydrogen peroxide such as the acid red dye LX6514 Pylakor is critical to the present invention for providing a distinct visual indication of an end point for terminating the bleaching operation. Guinea green and to a lesser extent phenolphthalein will function as redox color indicators by oxidizing during the bleaching treatment to cause a transformation from one color to another. Guinea green is a commercially available dye sold by the Aldrich Chemical Company having the chemical identity: ethyl [4-(p-[ethyl (m-sulfobenzyl) amnino]-alpha-phenylbenzylidene-2.5cyclohexadien-1-ylidene) (m-sulfobenzyl) ammonium hydroxide inner salt sodium salt. Guinea green causes the color of the teeth to appear green or bluish green and is bleached by the peroxide during the bleaching operation into a neutral color i.e. is neutralized to provide the absence of color over the duration of the bleaching operation. Upon neutralization the resulting color cannot be distinguished from the color of tooth enamel. Thus although the application of a redox color indicator which is oxidized by the bleaching operation is desirable in that it provides a color which will be eliminated as the bleaching operation proceeds it is the addition of a second dye which is pigment stable in peroxide which provides, in combination, greater control over the color transformation to a distinct new color identifying an end point for terminating the bleaching operation. The preferred second dye is the acid red dye LX6514 Pylakor of the chemical formula Acid violet 12 CAS #6625-46-3 and Acid Red 27 CAS#915-67-3. The acid red dye LX6514 Pylakor provides a red background color which becomes visible only when the dye guinea green is neutralized. Thus the user knows exactly when the bleaching treatment is satisfactorily completed. To accomplish this the redox color indicator should be predominant until the treatment is close to completion. Other pigment stable dyes that do not oxidize in a peroxide solution include Pylaklor Peacock Blue of the chemical formula Basic blue 9 CAS#8004-87-3, Pylaklor Yellow S-184 of the chemical formula Acid Yellow 17CAS#6359-98-4 & Acid Yellow 34CAS#6359-90-6 and Beet Powder 03600 Vegetable Color from Warner Jenkins Co and the like. Although any dye which is pigment stable in peroxide can be used the acid red dye LX6514 Pylakor is preferred. The red color is easily discernable against a white tooth surface. Moreover, a red color will absorb a significant amount of energy in the infra-red spectrum if a dental curing lamp, laser or heat lamp is applied and accelerate the release of oxygen when even shorter application time is deemed necessary. The preferred ratio of guinea green to the acid red dye is 4 to 1.

Components A and B of Table I are formulated as a gel-gel formulation. Alternatively, the components may be formulated as a liquid component and a dry component preferably in the form of a powder in a formulation as hereafter indicated in Table II:

TABLE II

| COMPONENT A (PEROXIDE LIQUID) | |
|---|---|
| Hydrogen Peroxide | 15–35% |

| COMPONENT B (ACTIVATOR) | |
|---|---|
| Constituent | Preferred Concentration in Parts by weight |
| Amorphous Fumed Silica | 10 |
| Manganese Citrate | 6 |
| Carbonate of Sodium | .2 |
| Guinea Green B.GA | .08 |
| Pylakor Acid Red LX6514 | .02 |

Component B is in the form of a powder. The composition of the powder/liquid bleach system as identified in Table II is substantially identical to the composition of Table I except for the use of a carbonate of sodium as the preferred pH alkaline buffer instead of an alkanolamine.

Both the gel-gel composition and the liquid powder composition can be dispensed through commercially available dispensers. The gel-gel composition can be dispensed in an automatically mixed proportion both accurately and safely so that it is convenient for the user. One simple method of mixing a gel-gel composition is to use two separate syringes. With this method equal or preferred amounts of each component can be easily and accurately placed on a mixing pad. Since both components are gels, there is no chance for spilling. Another method is to use a conventional static mixer for automatically mixing the two components in any desired preset ratio. This type of dispenser is well known for use in dispensing dental impression materials. Each component is separately stored in an individual compartment of the dispenser separated from one another and intermixed only upon use through a static mixing element attached to the discharge end of the dispenser. The dispenser can be used to dispense the mixed components directly upon the tooth or teeth to be bleached.

The preferred method of mixing the gel- gel as well as the powder liquid composition is to use a mixing capsule. In this configuration the liquid and powder can be each separately stored in a capsule separated by a membrane which is breakable by a manual movable member functioning as a plunger to open the membrane so as to cause the separated components to make contact with one another. Thereafter the cartridge can be place in an amalgamator for 3–6 seconds for throughly intermixing the components into a viscous gel. In this way the separate components i.e., the peroxide bleaching agent A and activator B can be pre-loaded in the factory into the capsule and sold to the dental practitioner for placement in a capsule dispensing syringe . This is ideally suited to the dentist or dental practitioner for use in the dental office with a 35% hydrogen peroxide bleaching constituent since all dentists have a dental amalgamator mixing device.

What I claim is:

1. A dental bleaching system composed of two separated components adapted to be dispensed from a single dispenser as a mixed viscous dental bleach composition comprising a first component having a viscous gel like consistency consisting essentially of hydrogen peroxide and fumed silica and a second component having a viscous gel like consistency comprising an aqueous composition including a gelling agent, catalyst, an alkaline pH buffer, a redox color indicator adapted to oxidize in the presence of a peroxide from a visible color into a neutralized color and a second dye stable in the presence of a peroxide with the concentration of the redox color indicator selected relative to the second dye such that the redox color will be predominant during the bleaching operation and the second dye will be predominant at the end of a controlled time period corresponding to when the bleaching treatment may be discontinued.

2. A dental bleaching system as defined in claim 1 wherein said redox color indicator is selected from the class consisting of ethyl [4-(p-[ethyl (m-sulfobenzyl) amino]-alpha-phenylbenzylidene-2.5cyclohexadien-1-ylidene) (m-sulfobenzyl) ammonium hydroxide inner salt sodium salt and phenolphthalein.

3. A dental bleaching system as defined in claim 2 wherein said second dye is selected from the group consisting of Pylakor Acid Red LX6514 of the chemical formula Acid violet 12 CAS #6625-46-3 and Acid Red 27 CAS#915-67-3 and Pylaklor Peacock Blue of the chemical formula Basic blue 9 CAS#8004-87-3, Pylaklor Yellow S-184 of the chemical formula Acid Yellow 17CAS#6359-98-4 & Acid Yellow 34CAS#6359-90-6 and Beet Powder 03600 Vegetable Color.

4. A dental bleaching system as defined in claim 3 wherein said gelling agent is fumed silica.

5. A dental bleaching system as defined in claim 4 wherein said catalyst is manganese citrate.

6. A dental bleaching system as defined in claim 5 wherein said pH buffer is an alkanolamine.

7. A dental bleaching system as defined in claim 6 wherein said second dye is Pylakor Acid Red LX6514.

8. A dental bleaching system as defined in claim 6 wherein the pH of said bleach composition is between 2.6 and 8.

9. A dental bleaching system as defined in claim 8 wherein the pH of said mixed dental bleach composition is between 4–7.

10. A dental bleaching system as defined in claim 1 wherein said first component consist of an aqueous hydrogen peroxide solution of between 10–35% and amorphous fumed silica in sufficient concentration to form a viscous gel consistency and with the second component consisting essentially of:

5–25% fumed silica,
5–15% manganese citrate,
0.2–5% triethanolamine,
0.2–5% sodium benzoate,
0.01 to 1% by volume of a redox color indicator unstable in peroxide selected from the class consisting of ethyl [4-(p-[ethyl (m-sulfobenzyl) amino]-alpha-phenylbenzylidene-2.5cyclohexadien-1-ylidene) (m-sulfobenzyl) ammonium hydroxide inner salt sodium salt and phenolphthalein,
0.01 to 0.5% by volume of a second dye stable in the presence of a peroxide selected from the group consisting of Pylakor Acid Red LX6514 of the chemical formula Acid violet 12 CAS #6625-46-3 and Acid Red 27 CAS#915-67-3 and Pylaklor Peacock Blue of the chemical formula Basic blue 9 CAS#8004-87-3, Pylaklor Yellow S-184 of the chemical formula Acid Yellow 17CAS#6359-98-4 & Acid Yellow 34CAS#6359-90-6 and Beet Powder 03600 Vegetable Color with water as the remainder of said second component in a sufficient amount to form a viscous gel consistency.

11. A dental bleaching system as defined in claim 10 wherein the concentration of said hydrogen peroxide constituent is 35%.

12. A dental bleaching system as defined in claim 10 wherein the concentration of said hydrogen peroxide constituent is 15%.

13. A method of dispensing a bleaching composition directly upon a tooth or teeth to be bleached comprising the steps of formulating a first component comprising hydrogen peroxide and a second component consisting essentially of a gelling agent, a pH alkaline buffer, a catalyst and a color indicator to provide a distinct visible color to the naked eye when the bleaching treatment may be terminated, placing each component in a capsule having two compartments separated by a membrane so that each component is isolated from each other, depressing a movable element in the capsule for breaking the membrane separating the compartments so that the components come into contact with one another, placing the capsule in a dental amalgamator to intermix the first and second components into a viscous gel consistency and placing the capsule in a dispensing syringe for dispensing the viscous gel directly onto the tooth or teeth to be bleached wherein said color indicator consists essentially of a redox color indicator adapted to oxidize in the presence of a peroxide from a visible color into a neutralized color and a second dye stable in the presence of a peroxide with the concentration of the redox color indicator selected relative to the second dye such that the redox color will be predominant during the bleaching operation and the second dye will be predominant at the end of a controlled time period corresponding to when the bleaching treatment may be discontinued.

14. A method of dispensing a bleaching composition directly upon a tooth or teeth to be bleached as defined in claim 13 wherein said redox color indicator is selected from the class consisting of ethyl [4-(p-[ethyl (m-sulfobenzyl) amino]-alpha-phenylbenzylidene-2.5cyclohexadien-1-ylidene) (m-sulfobenzyl) ammonium hydroxide inner salt sodium salt and phenolphthalein and said second dye is selected from the group consisting of Pylakor Acid Red LX6514 of the chemical formula Acid violet 12 CAS #6625-46-3 and Acid Red 27 CAS#915-67-3 and Pylaklor Peacock Blue of the chemical formula Basic blue 9 CAS#8004-87-3, Pylaklor Yellow S-184 of the chemical formula Acid Yellow 17CAS#6359-98-4 & Acid Yellow 34CAS#6359-90-6 and Beet Powder 03600 Vegetable Color.

15. A method of dispensing a bleaching composition directly upon a tooth or teeth to be bleached as defined in claim 13 wherein said first component is a liquid and said second component is a dry powder and said pH alkaline buffer is a carbonate.

16. A method of dispensing a bleaching composition directly upon a tooth or teeth to be bleached as defined in claim 13 wherein said first and second components have a gel consistency and wherein said pH alkaline buffer is a alkanolamine.

17. A method of automatically dispensing a bleaching composition directly upon a tooth or teeth to be bleached from a dual compartment dispensing syringe comprising the steps of formulating a first component consisting essentially of hydrogen peroxide and fumed silica in a viscous gel consistency and a second component consisting essentially of a silica gelling agent, an alkanolamine, a catalyst and a color indicator to provide a distinct visible color to the naked eye when the bleaching treatment has effectively terminated, said color indicator consisting essentially of a redox color indicator adapted to oxidize in the presence of a peroxide from a visible color into a neutralized color and a second dye stable in the presence of a peroxide with the concentration of the redox color indicator selected relative to the second dye such that the redox color will be predominant during the bleaching operation and the second dye will be predominant at the end of a controlled time period corresponding to when the bleaching treatment may be discontinued and with the second component concentration selected to form a gel consistency, placing each component in a separate compartment of a dual compartment dispensing syringe so that each component is isolated from each other, attaching a static mixer to the discharge end of the dispensing syringe, depressing each compartment of the dual compartment dispensing syringe so that the components are discharged simultaneously through the static mixer to cause the first and second components to intermix automatically from the dispensing syringe as it is dispensed directly onto the tooth or teeth to be bleached.

* * * * *